United States Patent
Enala

[19]

[11] Patent Number: 6,132,083
[45] Date of Patent: Oct. 17, 2000

[54] REAL-TIME MEASURING METHOD

[75] Inventor: Jarmo Enala, Ilmarinen, Finland

[73] Assignee: Aboatech Ltd., Turku, Finland

[21] Appl. No.: 08/817,834

[22] PCT Filed: Nov. 1, 1995

[86] PCT No.: PCT/FI95/00604

§ 371 Date: Jul. 31, 1997

§ 102(e) Date: Jul. 31, 1997

[87] PCT Pub. No.: WO96/14572

PCT Pub. Date: May 17, 1996

[30] Foreign Application Priority Data

Nov. 2, 1994 [FI] Finland ................................. 945168

[51] Int. Cl.⁷ .................................................. G01N 25/18
[52] U.S. Cl. ............................................................. 374/44
[58] Field of Search ................................. 374/31, 43, 44

[56] References Cited

U.S. PATENT DOCUMENTS

| | | | |
|---|---|---|---|
| 4,210,024 | 7/1980 | Ishiwatau et al. . | |
| 4,221,125 | 9/1980 | Oliver et al. | 73/61.46 |
| 4,735,082 | 4/1988 | Koloff | 73/25.03 |
| 4,852,027 | 7/1989 | Bowman et al. | 364/557 |
| 4,944,035 | 7/1990 | Aagardl Roger L. et al. | 364/556 |
| 5,237,523 | 8/1993 | Bonne et al. | 364/571.03 |
| 5,258,929 | 11/1993 | Tsuchida | 364/557 |
| 5,335,993 | 8/1994 | Marcus et al. | 374/11 |
| 5,346,306 | 9/1994 | Reading et al. | 374/10 |

FOREIGN PATENT DOCUMENTS

| | | | |
|---|---|---|---|
| 0189882 | 8/1986 | European Pat. Off. | 374/31 |
| 0576260 | 2/1996 | European Pat. Off. . | |
| 0251753 | 11/1991 | Japan | 374/43 |

Primary Examiner—Peter S. Wong
Assistant Examiner—Pia Tibbits
Attorney, Agent, or Firm—Ladas & Parry

[57] ABSTRACT

The invention relates to a real-time adaptive measuring method for determining the thermal conductivity K between a sensor and a medium, and/or for determining the thermal capacity C of the sensor and the temperature of the medium by means of the sensor that is in thermal exchange relation with the medium by changing the temperature of the sensor by means of supplying thermal power to the sensor and by measuring the thermal power supplied to the sensor. Therefore, it will be possible to distinguish between changes in the thermal power that are caused by a property of the medium and those caused by changes in the temperature of the medium.

6 Claims, 1 Drawing Sheet

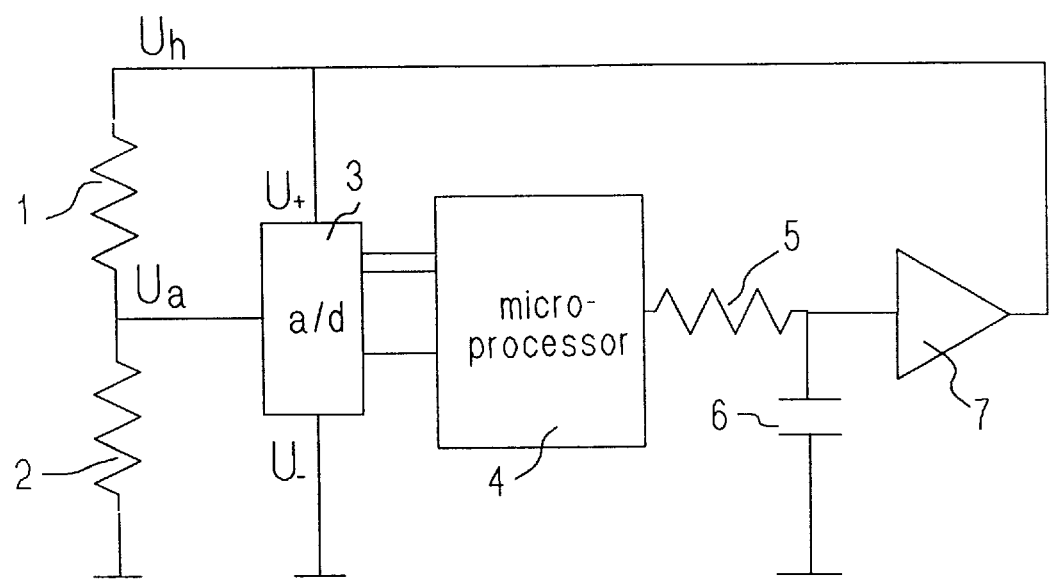

REAL-TIME MEASURING METHOD

BACKGROUND OF THE INVENTION

1. Field of the Invention

The invention relates to a real-time adaptive measuring method for determining the thermal conductivity K between a sensor and a medium. More particularly, the present invention is directed to determining thermal capacity C of a sensor and the temperature of a medium by means of the sensor when it is in a thermal exchange relation with the medium, by supplying thermal power to change the temperature of the sensor and by measuring the thermal power supplied to the sensor.

2. Description of Related Art

Known devices for measuring changes in thermal conductivity, for example, thermoanemometers, are based on the use of either one or two temperature elements. In devices utilizing two elements, one of the elements is heated and the power used for heating is simultaneously determined, whereas the other element is used to determine the temperature of the medium to be measured.

Devices utilizing two temperature elements fall into two groups. In one group, constant power is supplied to heat one element and the temperature difference between the two elements is measured. In a more common arrangement, the temperature difference between the elements is kept constant and the thermal power required for this purpose is measured. The latter method is advantageous in that the rate at which the device responds to changes in the quantity to be measured increases in proportion to the amplification of a feedback loop used for adjusting the temperature difference between the elements.

Devices utilizing one temperature element either measure the cooling or warming rate of the element or the thermal power required to maintain the sensor at a desired temperature. The former method corresponds to the method using two sensors, wherein constant power is supplied to heat one element and the temperature difference between the elements is measured. The latter method mainly corresponds to the method using two elements, wherein the temperature difference between the elements is kept constant and the thermal power required to keep it constant is measured. The problem with utilizing one element is that the temperature of the medium is not known, and so the power required to maintain the sensor at the desired temperature depends not only on the thermal conductivity of the medium but also, for example, on changes in the temperature of the medium, and these variables cannot be distinguished from one another.

U.S. Pat. No. 5,117,691 (the '691 patent) discloses a one-sensor measuring method that is based on differentiation and that operates without information about the surrounding temperature. In contrast, the invention according to the present application uses correlation checking, and determination of the temperature of the medium through calculation is an essential part of the method. Another significant difference from the method of the '691 patent is that the measurement takes place in real time. The method according to the present invention operates in real time, without the steady state that is required by the method described in the '691 patent and prevents its use for measurement in real time. The device according to the '691 patent can be implemented so that the temperature of the sensor need not stabilize and reach the steady state, but then the circuit uses a demodulator and measurement results still cannot be obtained in real time.

The problem with all the measuring devices utilizing two temperature sensors, such as these thermoanemometers, is the difficulty of maintaining their calibration over a wide temperature range. When a variable is determined using the temperature difference between two temperature sensors, their calibration must track very closely over the entire operating temperature range. Even when expensive precision components are used, this calibration still sometimes causes problems. For example the ageing of components, even the heat radiation or warming caused by the electronics themselves, can cause problems.

On the other hand, the problem with measuring devices utilizing one temperature element has been their slow response time. They are comparable to the conventional thermoanemometer that uses two temperature sensors and keeps the thermal power constant, measuring the temperature difference between the temperature sensors. In these conventional two-element thermoanemometers response time is shortened when the temperature difference between the temperature sensors is kept constant by adjusting the thermal power provided to heat the sensor. The speed of the thermoanemometer further increases in proportion to the amplification coefficient used in the adjustment. This has not been applicable lo devices having one sensor, since the temperature of the medium to be measured is not known and, as the temperature of the medium changes, keeping the temperature sensor at a constant temperature does not ensure that the temperature difference between the sensor and the medium remains constant.

In addition to their long response time, another problem with devices using one sensor is that in the method based on measuring the cooling rate of one sensor, the thermal capacity C of the sensor is assumed to be known, or at least constant. The signal-to-noise ratio is also poor, since the temperature difference between the sensor and the medium decreases during the measurement, but the noise level remains constant.

SUMMARY OF THE INVENTION

An object of the invention is to provide a method of measuring the temperature of a medium using one temperature sensor, that distinguishes between changes in the thermal power that are caused by a property of the medium to be measured, such as flow rate or moisture, and those changes in thermal power caused by changes in the temperature of the medium. Furthermore, it is possible to eliminate the precise relative calibration of the two temperature elements required in the conventional measurement method.

Another object is to provide a structure that is simpler and more economical than conventional structures.

Another object of the invention is to reduce the slowness of the conventional sensors using one temperature element, and eliminate the requirement that the thermal capacity of the sensor must be known beforehand or that at least it must be constant.

The method provided according to the invention is also adaptable, for a wide range of applications.

The invention is characterized by the appended claims, and the method according to the invention has the following advantages:

It can be practiced using a mechanically and electrically simple sensor comprising sensing one temperature element and two wires;

No relative difference in the calibration of sensor elements reduces its accuracy;

The sensor's calibration has good stability, because two elements are not used and, since the measurement is preferably performed by a microprocessor, the calibration can be performed by a software program. Including a small memory unit that is linked to each sensor element provides sensor-specific calibration data, so that different sensor elements can be substituted without any loss in precision, thus making maintenance easier;

Measurement results are obtained in real time, unlike conventional methods using one sensor;

The slowness of the sensor's thermal response is not very significant, (i.e. the ratio K/C is low). Thus the sensor can be made heavy and strong. For example, a rotation-symmetrical housing can be used so that the measurement result is independent of the direction of flow;

The material that can be measured is diverse. The medium surrounding the sensor can be a gas, vapour, liquid or solid, or a powder, foam, suspension or some other mixture of several phases;

The same device can be used to measure thermal conductivity and/or thermal capacity and temperature;

In the determination of thermal conductivity and thermal capacity, the method is insensitive to an error in the zero point of the temperature measurement;

In the determination of thermal conductivity and thermal capacity, the method is insensitive to the resistance of the coupling wires and the changes therein, so that the coupling wires can be long; and Since the method can be used to measure the thermal capacity of the sensor, the method can detect whether the sensor is contaminated, for example. It is also possible to correct the value determined for thermal conductivity with an amount proportional to the detected change in the thermal capacity, so that contamination of the sensor can be compensated in these calculations;

BRIEF DESCRIPTION OF THE DRAWING

In the following, the invention will be described in greater detail by means of examples and with reference to the accompanying drawing. The figure provided by the drawing is a schematic diagram of apparatus implementing the method according to the invention.

DETAILED DESCRIPTION OF A PREFERRED EMBODIMENT

In the figure, a voltage $U_a$ is used to heat a platinum resistor 2 (Pt 100) provided in the medium to be measured. The temperature of the resistor can be determined when the sensed voltage $U_a$ and the heating voltage $U_h$ are known. Since $U_a = U_h \cdot R_2/(R_2+R_1)$, the value of the sensor/resistor 2 and also its temperature can be calculated from that equation. A resistance value, such as $R_1=110\ \Omega$, approximating the resistance of the platinum resistor, is selected as the resistance of the resistor 1, which is in series with that platinum resistor. Thus, a change of a certain degree in the resistance of the platinum resistor corresponds to a change in the sensed voltage $U_a$ that is as great as possible. For the sake of simplicity, in this diagram the positive reference voltage $U_a$ of the A/D converter 3 is connected to the heating voltage $U_h$ and $U_a$ is connected to the earth so that the A/D converter 3 directly measures the ratio $U_a/U_h$.

A microprocessor 4 is provided that operates a software program that uses the resistance $R_2$ determined from the value of $U_a$ provided by the A/D converter 3 to determine the temperature $T_a$ of the platinum resistor 2, and compares $T_a$ with a desired value. If the temperature is too low, the program makes the signal at the output port of the microprocessor 4 connected to a low pass filter formed by a resistor 5 and a capacitor 6 increase. The output of the low pass filter controls an amplifier 7 supplying the heating voltage $U_h$. Correspondingly, if the temperature $T_a$ determined for the platinum resistor 2 is too high, the signal at the output port decreases so that the heating voltage $U_h$ decreases. With microprocessors presently well-known in the art, for example, this determination can easily be made hundreds of times per second so that, as practical matter, the measurement operation is continuous. The thermal conductivity and/or thermal capacity of the sensor can be calculated at the same frequency or at a frequency that is one decade lower, and other quantities such as the flow rate or moisture of the medium can also be calculated using those previously calculated quantities.

If a microprocessor that includes a D/A converter is used, the resistor 5 and the capacitor 6 are unnecessary and the analog output of the D/A converter of the processor can be used to directly control the amplifier 7. When a microprocessor including an A/D converter is used, an external A/D converter 3 is, naturally, unnecessary. If the capacity of the D/A converter of the processor to supply current is sufficient, the amplifier 7 can also be eliminated. In such a case the device according to the invention requires only three components: a microprocessor 4, a temperature element 2 and a resistor 1.

The voltage $U_h$ is known since the software sets its value. The resistance and the temperature response for the platinum resistor 2, i.e. the temperature sensor, is obtained from the A/D converter 3, so that the power $P_{tot}$ required for heating it can be calculated. When the temperature $T_a$ of the platinum resistor 2 is adjusted by the software program, the correlation of the thermal conductivity $K_c$ with this changing temperature $T_e$ is calculated, and a corrected value for the temperature estimate $T_c$ of the temperature of the medium $T_g$ can be determined.

Changing the heating voltage $U_h$ alters the temperature $T_a$ of the temperature sensor 2. Changes in the temperature $T_a$ may resemble a sine function, a saw tooth function, an exponential/rectangular function or some other periodic or aperiodic function, as a function of time, but the moving average of the sensor temperature $T_a$ may also slowly change in response to changes in the temperature of the medium $T_g$. Also, the difference between those two temperatures $T_a$ and $T_g$ can be selectively varied to change the precision of the measurement or to change the current consumption of the device.

Calculating the thermal conductivity $K_c$ repeatedly, using different temperature values, taking into account the change $P_k$ in the thermal power $P_{tot}$ required by the sensor caused by a change in the sensor temperature $T_a$, permits calculation of the thermal conductivity of the medium and a determination of the degree of correlation between the estimated thermal conductivity $K_c$ of the medium and the sensor temperature $T_a$ for each period. A correlation between $K_c$ and $T_a$ indicates a change in the temperature $T_g$ of the medium. New estimated values $T_c$ for the temperature $T_g$ of the medium are determined once during almost every temperature measurement cycle of the sensor. There is no need to wait for a sensor temperature $T_a$ to settle at a stable value. Even temporary values that occur while the sensor temperature is still changing are valid as measurement values, in accordance with the present invention, since the calculation algorithm used does not require a steady-state measured value.

Large changes in the temperature $T_g$ of the medium may produce erroneous values before the program is able to correct the temperature estimate $T_c$ used for the medium to a more suitable value. Such changes, however, can be compensated for by the software program so that the temperature estimate $T_c$ is adjusted by extrapolation before the next time the software program calculates the degree of correlation between $K_c$ and $T_a$.

The cause of a change in the power $P_k$ needed to maintain the temperature $T_a$ of the temperature sensor 2 may be either a change in the thermal conductivity K between the sensor and the medium, or a change in the temperature of the medium $T_g$, or both. A change of temperature of the medium $T_g$ is detected be the aforementioned correlation calculations, when they are performed sufficiently frequently. Any residual change in the power $P_k$ not attributed to a change in the temperature of the medium $T_g$ by these correlation checks, be attributed to a change in thermal conductivity K. Therefore this information about the temperature of the medium $T_g$ can also be utilized in the equation disclosed below for calculating thermal conductivity.

The example given above employs a platinum resistor because they are widely used and can be heated by current conducted directly through them. A nickel resistor, a piece of metal wire of arbitrary length, a film vaporized on a surface, a semiconductor component, or any other device having electrical properties that are a function of temperature, can also used. Alternatively, the component measuring the temperature and the component used to heat and/or cool it may be separate. For example, a combination of a platinum resistor and a heating resistor, or a combination of a semiconductor component and a Peltier element may be used. However, the thermal conductivity between the sensor components used for heating and for temperature measurement must be high. Alternatively, the temperature of the sensor may be measured externally, by detecting the infrared radiation the sensor produces, for example. The sensor also may be heated externally, by means of electromagnetic radiation, for example.

The following analysis assumes that the sensor is thermally connected to a medium. The medium may be a gas, vapour, liquid, solid or a heterogenous system formed by several phases, such as a sol, emulsion, aerosol, foam, or a macroscopic phase formed by two liquids, or a solid piece in a gas, wherein the piece has a surface to which the sensor is attached, or a fluid or gas flowing in a tube where, in accordance with the present invention, the flow rate is measured by a sensor attached to the exterior of the tube.

Thermal Conductivity (K)

If the temperatures $T_a$ and $T_g$ differ from one another, heat is transferred from the sensor to the medium at a power level $P_k$, which is proportionate to the product of the temperature difference $T_a-T_g$ between the sensor and the medium and the thermal conductivity K between the sensor and the medium. When the sensor is maintained at a certain temperature $T_a$, the following power level $P_k$ required for the purpose is:

$$P_k=K(T_a-T_g).$$

If the effect of a convection current is to be taken into account, a more complicated equation is used to relate $P_k$ to K, $T_a$ and $T_g$. This does not alter the principle of the invention. However, changing the temperature of the sensor then requires an additional power value $P_c$, which is proportionate to the product of the rate $dT_a/dt$ at which the temperature of the sensor changes and the thermal capacity C of the sensor C:

$$P_c=C\cdot dT_a/dt.$$

Thus, the total power to be supplied to the sensor $P_{tot}$ is:

$$P_{tot}=P_c+P_k=C\cdot dT_a/dt+K(T_a-T_g).$$

That is, the total power $P_{tot}$ consists of two parts $P_k$ and $P_c$, which are used to maintain the temperature of the sensor at a certain constant level, or to change it at a given rate. Since "power" refers to thermal power, this value will be a negative value if the sensor is at a lower temperature than the medium, or if the rate of change $dT_a/dt$ of the sensor temperature acquires a sufficiently high negative value. The total power $P_{tot}$ and the temperature $T_a$ of the sensor is measured at a given interval "t". The unknowns K, C and $T_g$ are determined using that equation.

According to the present invention, the temperature of the sensor $T_a$ is determined as a function of time, and the power $P_{tot}$ supplied to the sensor is adjusted over time so that the temperature of the sensor is maintained at a predetermined value as a function of time. Since the convection power $P_c$ is proportionate to the rate of changed $dT_a/dt$ of the sensor temperature $T_a$, and the conduction power $P_k$ to the temperature difference between the sensor and the medium $T_a-T_g$, selecting a suitable estimate $T_c$ for $T_g$ as a function of time permits a differentiation between the two aforementioned powers $P_c$ and $P_k$ and, thus, permits determination of both thermal conductivity and the thermal capacity of a system.

Correction for the Temperature of the Medium ($T_g$)

In order to understand how the calculation of the thermal conductivity K is corrected for the temperature of the medium $T_g$, determination of the thermal conductivity K is examined first. Each measurement of the temperature of the sensor $T_a$ provides an instantaneous value, such that $dT_a/dt=0$, and thus $P_c=0$, and $P_{tot}=P_k$. Consequently, in that instant:

$$P_{tot}=P_k+P_c=P_k=K(T_a-T_g)<=>K=P_k/(T_a-T_g).$$

However, the problem is that the temperature of the medium $T_g$ is not known. Nonetheless, the temperature $T_g$ of the medium can be given a value $T_c$ such that the following equation is true:

$$K_c=P_k/(T_a-T_c)$$

There, $K_c$ would be the value of the conductivity between the sensor and the medium K if the temperature of the medium $T_g$ were at the estimated value $T_c$. Then the equation $P_k=K(T_a-T_g)$ can be evaluated using the power value $P_k$ determined using $K_c$ so that the equation is as follows:

$$K_c=K\,(T_a-T_g)/(T_a-T_c)$$

Assuming that $T_a>T_g$, $T_c$, there are three different possibilities to consider:

if $T_c>T_g$ then the coefficient $(T_a-T_g)/(T_a-T_c)>1$,
thus $K_c>K$ and $(T_a-T_g)/(T_a-T_c)$ decreases when $T_a$ increases;

if $T_c=T_g$ then the coefficient $(T_a-T_g)/(T_a=T_c)=1$,
thus $K_c=K$ and $(T_a-T_g)/(T_a-T_c)$ is independent of $T_a$, if $T_c<T_g$ then the coefficient $(T_a-T_g)/(T_a-T_c)<1$,
thus $K_c<K$ and $(T_a-T_g)/(T_a-T_c)$ increases when $T_a$ increases.

Thus, if the correct value ($T_c=T_g$) is provided as the temperature estimate of the medium, the value $K_c$ calculated for the thermal conductivity K is correct, i.e., $K_c=K$ and $K_c$ is independent of $T_a$. If an incorrect value $T_c \neq T_g$ is provided as the temperature estimate, the value calculated for $K_c$ is inaccurate and is dependent on the temperature of the sensor $T_a$.

As shown above, that the accuracy of the estimate $T_c$ provided for the temperature of the medium $T_g$ as well as the direction of the required correction, can be inferred from the degree of correlation between the value $K_c$ calculated for thermal conductivity and the temperature $T_a$ of the sensor. Furthermore, that degree of correlation is a function of the size of the difference between the temperature estimate $T_c$ and the temperature of the medium $T_g$, similar results are obtained when $T_a < T_g$, $T_c$, thus in addition to the direction of the required correction, the amount of the correction can also be inferred from the degree of correlation as found in these calculations.

Changing the temperature of the sensor $T_a$ as a function of time and monitoring the value calculated for the thermal conductivity $K_c$ to determine its degree of correlation with the temperature of the sensor $T_a$, reveals whether the estimated temperature of the medium $T_c$ used in the calculation is correct. Again, if that estimate is incorrect, the direction and amount of the required correction are indicated by the size and sign of the correlation, as shown above.

Furthermore, when thermal capacity C of the sensor is known, thermal conductivity K can be determined even though the temperature of the sensor $T_a$ is changing. Since $T_a$ is known as a function of time, $dT_a/dt$ is also known in the following equation:

$$K_c = P_k/(T_a - T_c) = (P_{tot} - P_c)/(T_g - T_c) = (P_{tot} - C \cdot dT_a/dt)/(T_a - T_c)$$

Thus, all variables on the right side and K can be calculated in real time for any given point in time, if thermal capacity C is known.

If the measurement of the thermal conductivity K is the primary objective, and the degree of correlation between the sensor temperature for a sensor having a known capacity and the calculated thermal conductivity $K_c$ for the determined value of K is known, it is not necessary to correct the temperature of the medium. The error in the value $K_c$ calculated for the thermal conductivity can be directly corrected, because amount and direction of the required correction for this error in the value of $T_a$ are indicated by that degree of correlation, as shown above.

So long as $T_g$ of the medium changes relatively steadily during a given time period, a new estimated value can be extrapolated for the temperature of the medium $T_c$ by assuming that the rate of change occurring before the correlation between the temperature $T_a$ of the sensor and the value determined for the thermal conductivity $K_c$ was last calculated will continue at the same rate.

Determination of Thermal Capacity (C)

To determine the thermal capacity C of the sensor, the thermal conductivity K is first determined when the temperature of the sensor $T_a$ has a first measured value. The temperature of the sensor $T_a$ is then changed by an infinitesimally small amount $dT_a$ over a time interval dt, so that the total power is now:

$$C \cdot dT_a/dt = P_{tot} - K(T_a - T_g) \iff C = (P_{tot} - K(T_a - T_g))/(dT_a/dt) = (P_{tot} - P_k)/(dT_a/dt).$$

However, when the change $dT_a$ in the temperature of the sensor is very small, the value of $K(T_a - T_g) = P_k$ is constant. Then the expression $P_{tot} - P_k$ in the numerator is the difference between the power $P_{tot}$ that is required to adjust the temperature of the sensor in accordance with the value of $dT_a/dt$ and the power $P_k$ required to maintain the sensor at a constant temperature.

However, it is not necessary to know the thermal conductivity K when the thermal capacity C is being measured, since C can be determined in an alternative manner. If we assume that the temperature of the sensor changes by a infinitesimally small amount $dT_a$ during dt, then:

$$P_{tot.1} = P_c + P_k = C \cdot dT_a/dt + P_k$$

And if the temperature of the sensor $T_a$ is then changed at an equal rate in the opposite direction, then:

$$P_{tot.2} = C \cdot -dT_a/dt + P_k$$

Since $dT_a$ is infinitesimally small, $P_k$ is a constant value thus subtracting these equations produces:

$$P_{tot.1} - P_{tot.2} = C \cdot 2dT_a/dt \Rightarrow C = (P_{tot.1} - P_{tot.2})/(2dT_a/dt).$$

Thus the invention permits determination of both thermal conductivity K and thermal capacity C using the measured temperature $T_a$.

Uses of the Invention

The thermal conductivity of a medium can be charged by a change in flow conditions or in the properties of the medium itself and thermal capacity can be changed by contamination of the sensor as well as by a change in the properties of the medium. Thus the invention can be used for measuring the flow rate of a medium, for sensing contact, for determining moisture content, for measuring pressure, for measuring gas moisture, for measuring thermal properties through a tube wall, and also for determining the levels of materials inside containers.

Contact is sensed in accordance with the invention by providing a temperature sensor in contact with a material that has thermal conductivity and thermal capacity values that change when the surface of the material is touched. Contact can then be detected by the sensor, regardless of the temperature of the object that is touching that material. Similarly, an increase in moisture usually improves the thermal conductivity of a medium, but changes in the surrounding temperature do not affect the accuracy of measurements of the moisture in the medium. Useful applications of this invention for sensing moisture content include plant cultivation and monitoring the drying of structures, for example in connection with concrete construction and water damage.

On the other hand, when gas pressure increases, the thermal capacity of that gas increases. It is easiest to perform such a pressure measurement if the gas to be measured surrounds the sensor and is immobile, but the gas need not be immobilized. Instead, the sensor may include a measuring chamber that is connected to the gas pressure to be measured, via a capillary tube, for example. Measurement of gas moisture in accordance with the invention is provided by coating the sensor or filling the sensor's measuring chamber with a suitable hygroscopic material that absorbs more water as the atmospheric moisture content increases. Then the resulting change in the thermal capacity of the hygroscopic material is calculated to determine the moisture content of the gas. Alternatively, the thermal capacity of the hygroscopic material is maintained at a constant value by changing the temperature of the sensor, and the required temperature change is a function of moisture content of the gas.

On the other hand, King's law provides an approximation of $P_k$ for an object surrounded by a flowing medium, as follows:

$$P_k = K(T_a - T_g) = (C_o + C_l v^{1/2})(T_a - T_g)$$

where $C_o$ and $C_l$ are constants characteristic of the measuring apparatus and v is the flow rate of a medium. Then if thermal conductivity K is determined in the manner described above, the flow rate can be calculated from the formula:

$$v=[(K-C_o)/C_l]^2$$

Thus, King's law can be used to determine flow rate "v" in accordance with the present invention. King's Law can also be modified to take into account the turbulence, viscosity, moisture and pressure of the flowing medium, as is well-known in the art, for sensing these characteristics of the flow using the principle of this invention.

Measurements through a Tube Wall

The invention is also well-suited to measuring the flow rate of a material in a tube through the tube wall. For this purpose, the sensor is in thermal contact with the tube wall, so that the tube wall has approximately the same temperature as the sensor $T_a$. This measurement corresponds to those described above, except that heat is also transferred between the sensor and the surroundings, in addition to being transferred between the medium and the sensor, since the sensor is not entirely surrounded by the medium. This additional heat transfer is represented by the power value $P_v$. Except for this additional term $P_v$ which is added to the other components of the total power $P_{tot}$, the calculation is the same as for a sensor that is entirely surrounded by the medium.

Flow measurement through the tube wall provides convenience for post-assembly measurements and system maintenance operations. Also, the measurement system is durable and it does not affect the flow of the material in the tube. Furthermore, measurement through the tube wall can also estimate the amount of contamination gathering on the inner surface of a tube, by measuring changes in thermal capacity.

Thermal properties can be measured through a tube wall in accordance with the present invention by thermally connecting the sensor to the tube wall. The tube should have good thermal conductivity between the inner and outer surfaces of the wall but poor thermal conductivity in the direction of the length of the tube, for example tubes with thin walls and tubes of thermally anisotropic material. In these tubes, heat tends to be transferred between the sensor and the medium to be measured, so that it is easy to measure the thermal properties of the medium. For example, an increase in the flow of the medium increases its thermal conductivity, which can be measured in accordance with the invention.

Contaminants attached to the interior of the tube change the thermal capacity of the tube and are also detectable in accordance with the invention. Since the ratio C/K is often a large value for measurements taken when such contaminants are present, conventional measuring methods that use a single temperature element and measure the cooling rate to determine flow rate are difficult to apply, because of the resulting slowness of the response provided by the measuring system.

An increase in container surface temperature relative to the temperature of the sensor changes the detected thermal conductivity value. The initial temperature of its contents does not affect the measurement of thermal conductivity, and so, this measurement is possible even through the container's wall. Similarly, macroscopic liquid phases can be distinguished by detecting the thermal conductivity of the liquid flowing past the sensor. For example, the macroscopic liquid phases may be a lubricating oil that became mixed with water during a disturbance in its flow.

Since the slowness of the thermal response provided by the sensor is not very significant to the measurement values provided by the sensor in accordance with the present invention, that sensor can have a robust structure. For example a spherical housing can be used so that, with sufficiently thin wiring and proper suspension, the sensor provided in accordance with the present invention can be made fully independent of the direction of the flow, rather than just being independent in one plane as it is when a tubular housing is used. The temperature sensitivity of a symmetrical housing enclosing the element, and if it is made of a very heat conductive material such as aluminum, aluminum oxide, copper or silver, is the same everywhere. Thus, because of the geometry of the housing, no one direction of flow differs from any other and the sensor is insensitive to changes in the direction of flow. Whereas, it is impossible for a measuring device that requires two temperature sensor elements to achieve this symmetry in three dimensions, even if ideal temperature sensor elements could be used.

The circuit according to the invention can be implemented in different ways, but the combinations described herein have been kept simple, in order to illustrate the principle of the invention. It will be apparent to one skilled in the art, that variations and modifications of these embodiments are possible within the scope of the described invention. The scope of the invention is defined by the appended claims.

What is claimed is:

1. A method for determining thermal conductivity between a sensor and a medium in a thermal exchange relation with the sensor, said method comprising the steps of:

measuring the temperature of the sensor;

supplying thermal power to the sensor to raise the temperature thereof;

measuring the thermal power supplied to the sensor;

measuring the raised temperature of the sensor due to supplying the thermal power thereto;

estimating a temperature of the medium due to thermal exchange with the sensor;

estimating a value of thermal conductivity between the sensor and the medium based on the estimated temperature of the medium and the measured thermal power supplied to the sensor; and correcting the estimated value of thermal conductivity, if necessary, based on a correlation between the thermal conductivity and the temperature of the sensor.

2. A method as claimed in claim 1, wherein the temperature of the sensor increases upon supply of said thermal power according to a time dependent temperature function and said estimated value of thermal conductivity being correlated with the temperature of the sensor as it increases according to said time dependent temperature function.

3. A method as claimed in claim 2, which comprises calculating thermal capacity of said sensor by comparing the rate of change of the temperature of the sensor, due to the supplied thermal power, and said time dependent temperature function.

4. A method as claimed in claim 3, comprising modifying the corrected value of the thermal conductivity to take into account any change in thermal capacity of said sensor due to surface irregularity thereof.

5. A method as claimed in claim 2, comprising controlling the time dependent temperature function of the sensor to assume a determined value.

6. A method as claimed in claim 1, comprising changing the estimated temperature of the medium, if necessary, to an actual value of the temperature of the medium on the basis of the corrected value of the thermal conductivity.

* * * * *